United States Patent [19]

Bresson et al.

[11] Patent Number: 4,514,293

[45] Date of Patent: Apr. 30, 1985

[54] ORE FLOTATION AND FLOTATION AGENTS FOR USE THEREIN

[76] Inventors: Clarence R. Bresson; Harold W. Mark, both c/o French, Hughes and Doescher, P.O. Box 2443, Bartlesville, Okla. 74005

[21] Appl. No.: 608,826

[22] Filed: May 10, 1984

[51] Int. Cl.[3] .................... B03D 1/06; C07C 154/02; C09K 3/00; C22B 3/00

[52] U.S. Cl. .................................. 209/167; 209/166; 252/61; 260/455 B; 568/69

[58] Field of Search .................. 252/61; 209/166, 167; 260/455 B; 568/69

[56] References Cited

U.S. PATENT DOCUMENTS

| | | | |
|---|---|---|---|
| 2,197,964 | 4/1940 | Bishop | 260/455 B |
| 3,660,412 | 5/1972 | Haugwitz | 260/455 B |
| 4,136,020 | 1/1979 | Fischer | 252/61 |
| 4,410,439 | 10/1983 | Crozier | 252/61 |

*Primary Examiner*—Paul Lieberman
*Assistant Examiner*—Robert A. Wax

[57] ABSTRACT

Ammonium N-carboxyalkyl-S-carboalkoxy dithiocarbamates, alkali metal N-carboxyalkyl-S-carboalkoxy dithiocarbamates, their use as flotation agents, and a process for the production of these novel compositions are disclosed.

19 Claims, No Drawings

ORE FLOTATION AND FLOTATION AGENTS FOR USE THEREIN

This invention relates generally to novel chemical compositions. In one respect, the invention relates to a process for making such compositions. In another aspect, the invention relates to ore flotation processes employing such novel compositions.

Froth flotation is a process for recovering and concentrating minerals from ores. In a froth flotation process the ore is crushed and wet ground to obtain a pulp. Additives such as mineral flotation or collecting agents, frothing agents, suppressants, stabilizers, etc. are added to the pulp to assist in separating valuable minerals from the undesired or gangue portions of the ore in subsequent flotation steps. The pulp is then aerated to produce a froth at the surface. The minerals which adhere to the bubbles or froth are skimmed or otherwise removed and separated. Selective suppressants or depressants inhibit the adherence of certain minerals to the bubbles or froth thus assisting in the separation of the froth product from the reject product which includes those minerals suppressed by the suppressant agent. The froth product or the reject product or both can then be further processed to obtain the desired minerals, such as by additional flotation stages. Generally the ore is initially floated to produce a rougher concentrate, the rougher concentrate thereafter being refloated in the presence of suppressants to further separate the minerals therein. Typical mineral flotation collectors include xanthates, amines, alkyl sulfates, arenes, sulfonates, dithiocarbamates, dithiophosphates, and thiols.

It is known from the art that some organic derivatives of trithiocarbonic acid are useful as flotation agents. U.S. Pat. No. 1,659,396, for instance, describes diethyltrithiocarbonate and the production thereof. U.S. Pat. No. 3,166,580 describes dicyclopentyl trithiocarbonates and their production as well as the utility of these compounds as flotation agents.

It is a continuing goal in the ore-processing industry to increase the productivity of ore flotation processes and, above all, to provide specific procedures which are selective to one ore or metal over other ores or metals present in the treated material.

It is an object of this invention to provide a novel composition of matter. Another object of this invention is to provide new dithiocarbamates. A further object of this invention is to provide a process for producing such new dithiocarbamates.

Yet another object of this invention is to provide an improved ore flotation process wherein such new dithiocarbamates are used as flotation agents.

Still another object of this invention is to provide a novel suppressant suitable for use in an ore flotation process.

These and other objects, advantages, details, features and embodiments of this invention will become apparent to those skilled in the art from the following detailed description of the invention and the appended claims.

In accordance with this invention it has been found that ammonium N-carboxyalkyl-S-carboalkoxy dithiocarbamates and alkali metal N-carboxyalkyl-S-carboalkoxy dithiocarbamates are novel compositions and are very effective ore flotation agents.

Thus, in accordance with a first aspect of this invention, novel compositions of matter are provided which can be characterized by the formula

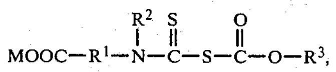

wherein M is selected from the group consisting of ammonium and alkali metals from Group IA of the Periodic Table of the Elements, $R^1$ is selected from the group consisting of alkylene radicals, $R^2$ is selected from the group consisting of H, and alkyl radicals, and $R^3$ is selected from the group consisting of alkyl and alkenyl radicals.

In accordance with another aspect of this invention there is provided a process for producing a composition having the formula

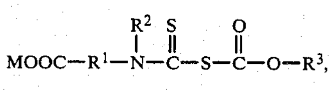

(I)

wherein M is selected from the group consisting of ammonium and alkali metals from Group IA of the Periodic Table of the Elements, $R^1$ is selected from the group consisting of alkylene radicals, $R^2$ is selected from the group consisting of H, and alkyl radicals, and $R^3$ is selected from the group consisting of alkyl and alkenyl radicals, which process comprises reacting a hydroxide having the formula $$MOH \quad (II),$$

wherein M is selected from the group consisting of ammonium and alkali metals from Group IA of the Periodic Table of the Elements, with $CS_2$ and an acid having the formula

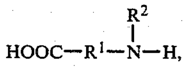

(III)

wherein $R^1$ is selected from the group consisting of alkylene radicals, and $R^2$ is selected from the group consisting of H and alkyl radicals, to form

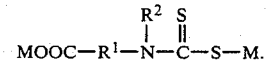

(IV)

The process further comprises reacting the product of formula (IV) with a haloformic ester having the formula

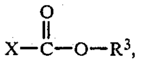

(V)

wherein X is selected from the group consisting of Cl, Br, and I, and $R^3$ is selected from the group consisting of alkyl and alkenyl radicals, to form the novel composition having the formula (I). The process further includes recovering the thus formed composition having the formula (I) as the product of the process.

Suitable acids represented by the formula (III) above include, but are not limited to the amino acids such as, for example, glycine, alpha-alanine, beta-alanine, alpha-aminoisovaleric acid, alpha-amino-n-caproic acid and the like.

The detailed operating conditions for the individual steps are not critical and specific values for the steps can be seen from the following examples. Generally, the first step of the reaction, namely the reaction of the acid, such as an amino acid, and the ammonium hydroxide or alkali metal hydroxide and $CS_2$, is carried out in an aqueous environment and at a temperature in the range from about 25° C. to about 100° C. and under a pressure of from about 0 to about 500 psig. The reaction time for this first step is somewhat dependent upon the other reaction conditions but will generally be in the range of from about 1 to about 4 hours.

The reaction of the product of formula (IV) with the haloformic ester of formula (V) will generally be carried out by a slow addition of the two compounds and mixing. The exothermic reaction is generally carried out at a temperature in the range from about 25° C. to about 100° C. and at a pressure in the range from about 0 to about 500 psig. for a time in the range from about 1 to about 10 hours.

The separation of the product of formula (I) can be carried out by standard techniques.

A further aspect of this invention resides in an ore flotation process. More specifically, such further aspect of this invention resides in a process for separating valuable ore materials from gangue materials. The ore flotation process of this invention distinguishes over the known ore flotation processes primarily in the employment of a new flotation agent to be defined. Otherwise, the recovery process involves crushing of the ore and ore grinding preparatory to mixing the thus ground ore and water to obtain a pulp. In this pulp the flotation agent is incorporated and the pulp is aerated to produce a froth at the surface which is rich in valuable ore materials but depleted of the gangue materials or vice versa. The ore materials, optionally, after additional flotation or frothing steps in which the novel flotation agent can be employed, are recovered. In addition to the novel flotation agent of the present invention, frothing agents, other selective suppressants, collectors, promoters and stabilizers which are known in the art can be used in the various steps. Generally the novel suppressant of the present invention will be advantageously employed in the flotation of a rougher concentrate following the use of a collector in a prior flotation step wherein Mo, Cu, Fe, etc. are separated as the rougher concentrate from the gangue materials in the core.

The compositions useful as flotation agents in the ore flotation process of this invention are characterized by the formula

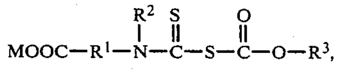

wherein M is selected from the group consisting of ammonium and alkali metals from Group IA of the Periodic Table of the Elements, $R^1$ is selected from the group consisting of alkylene radicals, $R^2$ is selected from the group consisting of H, and alkyl radicals, and $R^3$ is selected from the group consisting of alkyl and alkenyl radicals.

It is presently preferred that the alkylene radicals of $R^1$ each have no more than 4 carbon atoms, that the alkyl radicals of $R^2$ each have no more than 2 carbon atoms, and that the alkyl or alkenyl radicals of $R^3$ each have no more than 6 carbon atoms. The alkylene radicals of $R^1$, the alkyl radicals of $R^2$ and the alkyl or alkenyl radicals of $R^3$ can be linear or branched. Examples of such compounds useful as flotation agents in the process of this invention are those generally characterized as ammonium N-carboxyalkyl-S-carboalkoxy dithiocarbamates and alkali metal N-carboxyalkyl-S-carboalkoxy dithiocarbamates, such as, for example, Sodium N-carboxymethyl-S-carboethoxy dithiocarbamate, Ammonium N-carboxymethyl-S-carboethoxy dithiocarbamate, Potassium N-carboxymethyl-S-carboethoxy dithiocarbamate, Lithium N-carboxymethyl-S-carboethoxy dithiocarbamate, and the like, and mixutres of any two or more thereof. The presently preferred composition used as the flotation agent in the process of this invention is sodium N-carboxymethyl-S-carboethoxy dithiocarbamate.

The amount of ammonium N-carboxyalkyl-S-carboalkoxy dithiocarbamate and/or alkali metal N-carboxyalkyl-S-carboalkoxy dithiocarbamate employed in the mineral recovery process of this invention is not critical. The quantity will depend upon the process parameters. Generally, the novel ore flotation agent compositions of the present invention will be employed in the ore flotation mineral recovery process at concentration levels sufficient to provide the desired suppressant (or depressant) action on certain minerals. The amount of ammonium N-carboxyalkyl-S-carboalkoxy dithiocarbamate and/or alkali metal N-carboxyalkyl-S-carboalkoxy dithiocarbamate employed as a suppressant in the mineral recovery process of this invention will generally range from about 0.005 lb to about 10 lb of the ammonium N-carboxyalkyl-S-carboalkoxy dithiocarbamate and/or alkali metal N-carboxyalkyl-S-carboalkoxy dithiocarbamate per ton of solids or crushed ore, and more preferably range from about 0.1 to about 6 lb/ton of solids or crushed ore. The novel suppressants or depressants of the present invention can be added to an ore flotation meneral recovery process or system at the ore-grinding stage, the ore flotation step and/or to the concentrate which is to be further floated.

Various flotation agents or processing aids can be used in conjunction with the novel suppressants of the present invention such as, for example, flocculents, frothers, dispersants, promoters and the like.

It is generally believed that the novel dithiocarbamate compositions disclosed herein are useful for separating any valuable metal sulfide from its corresponding gangue material. It is also understood that the novel dithiocarbamates can facilitate the separation of a mixture of metals that are contained in a particular mining deposit or ore, said mixture being further separated by subsequent froth flotations or any other conventional separating methods. The dithiocarbamates herein disclosed are particularly useful as copper, nickel and/or iron suppressants in the separation of such minerals as molybdenum from the total ore. Examples of such molybdenum-bearing ores include, but are not limited to such materials as Molybdenum-Bearing ores:
- Molybdenite: $MoS_2$
- Wulfenite: $PbMoO_4$
- Powellite: $Ca(Mo,W)O_4$
- Ferrimolybdite: $Fe_2Mo_3O_{12}.8H_2O$ Other metal bearing ores within the scope of this invention are, for example, but are not limited to, such materials as Copper-bearing ores:
- Covellite: CuS
- Chalcocite: $Cu_2S$
- Chalcopyrite: $CuFeS_2$
- Bornite: $Cu_5FeS_4$
- Cubanite: $Cu_2SFe_4S_5$
- Valerite: $Cu_2Fe_4S_7$ or $Cu_3Fe_4S_7$
- Enargite: $Cu_3(As,Sb)S_4$
- Tetrahedrite: $Cu_3SbS_2$
- Tennanite: $Cu_{12}As_4S_{13}$
- Cuprite: $Cu_2O$
- Tenorite: CuO
- Malachite: $Cu_2(OH)_2CO_3$
- Azurite: $Cu_3(OH)_2CO_3$
- Antlerite: $Cu_3SO_4(OH)_4$
- Brochantite: $Cu_4(OH)_6SO_4$
- Atacamite: $Cu_2Cl(OH)_3$
- Chrysocolla: $CuSiO_3$
- Famatinite: $Cu_3(Sb,As)S_4$
- Bournonite: $PbCuSbS_3$ Lead-Bearing ore:
- Galena: PbS Antimony-Bearing ore:
- Stibnite: $Sb_2S_3$ Zinc-Bearing ores:
- Sphalerite: ZnS
- Zincite: ZnO
- Smithsonite: $ZnCO_3$ Chromium-Bearing ores:
- Daubreelite: $FeSCrS_3$
- Chromite: $FeO.Cr_2O_3$ Iron-Bearing ores:
- Pyrite or Marcasite: $FeS_2$
- Pyrrhotite: $Fe_5S_6$ to $Fe_{16}S_{17}$ Nickel-Bearing ores:
- Pentlandite: (FeNi)S
- Millerite: NiS
- Niccolite: NiAs The presently preferred ores in connection with which the process of this invention is applied are molybdenum, lead, copper and iron ores or minerals.

SEPARATION CONDITIONS

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of the inventive sodium N-carboxymethyl-S-carboethoxy dithiocarbamate. To a 1 Liter 3-neck flask fitted with a stirrer, thermometer, dropping funnel and reflux condenser was added 270 milliliters of water and 84 grams (2.1 moles) of sodium hydroxide pellets. After the pellets had dissolved and the temperature had dropped below 30° C., there was added 75.07 grams (1.0 mole) of glycine and allowed to stir until the temperature had again dropped below 30° C. To this mixture was added dropwise 76.14 grams (1.0 mole) of carbon disulfide which appeared to react slowly with the glycine salt since very little temperature increase was observed. After about 3 hours stirring at ambient room temperature there was added to the mixutre 108.5 grams (1.0 mole) of ethyl chloroacetate dropwise at which time the temperature slowly rose to about 45° C. with some refluxing, presumably carbon disulfide. During the ethyl chloroacetate addition, the color of the mixture turned from a bright red to yellow with a slight white precipitate and finally back to a dark red color. Extra water (613 milliliters) was added to dissolve the white precipitate, presumably NaCl. Thus, the reaction product solution was assumed to be a 20 weight percent solution of essentially sodium N-carboxymethyl-S-carboethoxy dithiocarbamate.

EXAMPLE II

This example describes the procedure used to evaluate the reaction product mixture from Example I as a suppressant in ore flotation. About 750 grams of a Cu/Ni/Fe-containing ore (Falconbridge ore) along with 300 milliliters of tap water and 0.5 grams (1.3 lb/ton) of lime was added to a ball mill and ground for 2 minutes and 52 seconds. The ground mixture was transferred to a 2.5 Liter capacity Denver D-12 flotation cell along with enough water to make about a 30 weight percent aqueous slurry. Also added was 6 drops (0.068 lb/ton) of a frother (Dowfroth 250) and 6 milliliters (0.16 lb/ton) of a 1 weight percent aqueous solution of sodium isopropyl xanthate and the slurry conditioned for 1 minute. After conditioning, the slurry was floated for 7 minutes and the concentrate filtered, dried and analyzed. The procedure was repeated and an average weight percent recovery estimated. In this manner there was obtained average weight recoveries of 89.2 percent Cu, 78.6 percent Ni, and 57.1 weight percent Fe.

The procedure was again repeated except that no lime was added to the grind step, 10 weight aqueous sulfuric acid was added during the conditioning step to adjust pH from 9 to 6, and in addition to the xanthate collector there was added 1.7 milliliters (5 lbs/ton) of a 20 weight percent aqueous solution of sodium N-carboxymethyl-S-carboethoxy dithiocarbamate prepared as described in Example I. The mixture was conditioned for 1 minute and floated for 7 minutes. The concentrate was filtered, dried and analyzed to determine whether the dithiocarbamate acted as a suppressant, collector, or had no affect. These results are listed in Table I where it can be seen that the inventive dithiocarbamate ester (run 2) suppressed the flotation of Cu, Ni and Fe when compared to the control where only the xanthate reagent (run 1) was used.

TABLE I

Reagent Suppressant Action (Falconbridge Ore)

| Run | Reagent (s) | lb/ton | Av. Wt. % Recovery Cu | Ni | Fe |
|---|---|---|---|---|---|
| | Control: | | | | |
| 1 | Sodium Isopropyl Xanthate | 0.16 | 89.2 | 78.6 | 57.1 |
| | Invention: | | | | |
| 2 | Sodium Isopropyl Xanthate plus | 0.16 | 56.7 | 53.6 | 32.0 |

TABLE I-continued

Reagent Suppressant Action (Falconbridge Ore)

| Run | Reagent (s) | lb/ton | Av. Wt. % Recovery Cu | Ni | Fe |
|---|---|---|---|---|---|
| | Sodium N—carboxymethyl-S—carboethoxy dithiocarbamate | 5.0 | | | |

In summary, the data herein disclosed reveal that the novel ammonium N-carboxyalkyl-S-carboalkoxy dithiocarbamates and alkali metal N-carboxyalkyl-S-carboalkoxy dithiocarbamates are useful as ore flotation agents. These compounds are particularly suited for suppressing copper, nickel, and iron in ore flotation processes.

Reasonable variations and modifications which will become apparent to those skilled in the art can be made in this invention without departing from the spirit and scope thereof.

We claim:

1. The composition represented by the formula

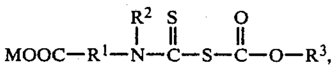

wherein M is selected from the group consisting of ammonium and alkali metals, $R^1$ is selected from the group consisting of alkylene radicals each having no more than 4 carbon atoms, $R^2$ is selected from the group consisting of H, and alkyl radicals each having no more than 2 carbon atoms, and $R^3$ is selected from the group consisting of alkyl and alkenyl radicals each having no more than 6 carbon atoms.

2. A composition in accordance with claim 1 wherein M is sodium.

3. A composition in accordance with claim 2 wherein $R^1$ is a methylene radical, $R^2$ is H, and $R^3$ is an ethyl radical.

4. Sodium N-carboxymethyl-S-carboethoxy dithiocarbamate.

5. A process for producing a composition having the formula

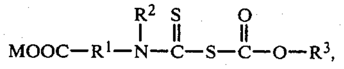

(I)

wherein M is selected from the group consisting of ammonium and alkali metals, $R^1$ is selected from the group consisting of alkylene radicals each having no more that 4 carbon atoms, $R^2$ is selected from the group consisting of H, and alkyl radicals each having no more than 2 carbon atoms, and $R^3$ is selected from the group consisting of alkyl and alkenyl radicals each having no more than 6 carbon atoms, comprising the steps of:

(a) reacting a hydroxide having the formula

MOH (II), wherein M is selected from the group consisting of ammonium and alkali metals, with $CS_2$ and an acid having the formula

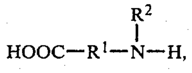

(III)

wherein $R^1$ is selected from the group consisting of alkylene radicals each having no more than 4 carbon atoms, and $R^2$ is selected from the group consisting of H and alkyl radicals each having no more than 2 carbon atoms, to form

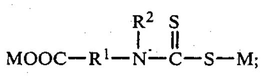

(IV)

(b) reacting the product of formula (IV) with a haloformic ester having the formula

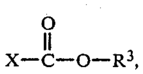

(V)

wherein X is selected from the group consisting of Cl, Br, and I, and $R^3$ is selected from the group consisting of alkyl and alkenyl radicals each having no more than 6 atoms, to form a composition having the formula (I); and (c) recovering said thus formed composition as the product of the process.

6. A process in accordance with claim 5 wherein X is Cl.

7. A process in accordance with claim 5 wherein M is sodium.

8. A process in accordance with claim 5 wherein $R^1$ is a methylene radical.

9. A process in accordance with claim 5 wherein $R^2$ is H.

10. A process in accordance with claim 5 wherein $R^3$ is an ethyl radical.

11. A process in accordance with claim 10 wherein X is Cl.

12. A process in accordance with claim 11 wherein $R^1$ is a methylene radical and $R^2$ is H.

13. A process in accordance with claim 5 wherein M is sodium, $R^1$ is a methylene radical, $R^2$ is H, and $R^3$ is an ethyl radical.

14. A process in accordance with claim 13 wherein X is Cl.

15. A process for recovering minerals comprising:

(a) mixing crushed ore containing minerals, water and a composition having the formula

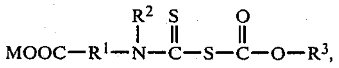

(I)

wherein M is selected from the group consisting of ammonium and alkali metals from, $R^1$ is selected from the group consisting of alkylene radicals each having no more than 4 carbon atoms, $R^2$ is selected from the group consisting of H, and alkyl radicals each having no more than 6 carbon atoms, and $R^3$ is selected from the group consisting of alkyl and alkenyl radicals, to establish a pulp;

(b) aerating said thus established pulp to produce a froth containing said minerals; and (c) recovering said minerals from said thus produced froth.

16. A process in accordance with claim 15 wherein M is sodium.

17. The composition produced by the process of claim 5.

18. A process for recovering minerals comprising:

(a) mixing crushed ore containing minerals, water and a composition produced in accordance with the process of claim 5 to establish a pulp;

(b) aerating said thus established pulp to produce a froth containing at least a portion of said minerals; and (c) recovering said minerals from said thus produced froth.

19. A process for recovering minerals comprising:

(a) mixing a rougher concentrate containing said minerals, water and a composition produced in accordance with the process of claim 5 to establish a pulp;

(b) aerating said thus established pulp to produce a froth containing at least a portion of said minerals; and (c) recovering said minerals from said thus produced froth.

* * * * *

UNITED STATES PATENT AND TRADEMARK OFFICE

CERTIFICATE OF CORRECTION

PATENT NO. : 4,514,293

DATED : April 30, 1985

INVENTOR(S) : Clarence R. Bresson et al

It is certified that error appears in the above-identified patent and that said Letters Patent is hereby corrected as shown below:

Add to page one of the patent: Assignee: Phillips Petroleum Company
Bartlesville, Oklahoma

Signed and Sealed this

*Twenty-ninth* Day of *October 1985*

[SEAL]

*Attest:*

DONALD J. QUIGG

*Attesting Officer*

*Commissioner of Patents and Trademarks—Designate*